United States Patent
Wiktor

(10) Patent No.: US 9,314,560 B2
(45) Date of Patent: Apr. 19, 2016

(54) APPARATUS FOR HEATING A MEDICAL FLUID

(75) Inventor: Christoph Wiktor, Gelnhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 625 days.

(21) Appl. No.: 13/493,372

(22) Filed: Jun. 11, 2012

(65) Prior Publication Data
US 2012/0323169 A1  Dec. 20, 2012

Related U.S. Application Data

(60) Provisional application No. 61/497,149, filed on Jun. 15, 2011.

(30) Foreign Application Priority Data

Jun. 15, 2011  (DE) .......................... 10 2011 104 218

(51) Int. Cl.
  *A61M 1/16*  (2006.01)
  *A61M 5/44*  (2006.01)
(52) U.S. Cl.
  CPC ........... *A61M 1/1656* (2013.01); *A61M 1/1664* (2014.02); *A61M 5/44* (2013.01); *A61M 2205/127* (2013.01); *A61M 2205/3334* (2013.01); *A61M 2205/3653* (2013.01); *A61M 2205/3673* (2013.01); *A61M 2205/3686* (2013.01)
(58) Field of Classification Search
  CPC . A61M 5/44; A61M 5/445; A61M 2205/365; A61M 1/1664; A61M 2205/3334; A61M 2205/3653; F24H 9/2028; F24H 1/142
  USPC .......... 392/466, 467, 468, 469, 470; 604/114, 604/113, 6.13, 291
  See application file for complete search history.

(56) References Cited

U.S. PATENT DOCUMENTS

| | | | |
|---|---|---|---|
| 4,356,383 A | 10/1982 | Dahlberg et al. | |
| 5,437,673 A * | 8/1995 | Baust et al. | ..................... 606/23 |
| 6,743,201 B1 | 6/2004 | Doenig et al. | |
| 2003/0220598 A1 * | 11/2003 | Busby et al. | ................. 604/5.01 |
| 2005/0008354 A1 | 1/2005 | Cassidy | |

(Continued)

FOREIGN PATENT DOCUMENTS

| | | |
|---|---|---|
| CN | 1094605 | 11/1994 |
| DE | 10 2008 038 097 | 2/2010 |

(Continued)

*Primary Examiner* — Kami A Bosworth
*Assistant Examiner* — Hamza Darb
(74) *Attorney, Agent, or Firm* — Jacobson Holman, PLLC

(57) ABSTRACT

An apparatus for heating a medical fluid includes a fluid passage for delivering the medical fluid, a heating element for heating the medical fluid, and a detector. The detector has a first detector for detecting a parameter which correlates with a flow rate of the medical fluid, or a second detector for detecting a parameter which corresponds to a set point, for the flow rate of the medical fluid. A controller controls regulates a temperature of the medical fluid in the fluid passage and a temperature of the heating element, and a switching circuit switches the controller between controlling or regulating the temperature of the medical fluid and controlling or regulating the temperature of the heating element. The switching circuit is configured such that the switching is triggered in response to the switching circuit detecting that the flow rate falls below or exceeds a predetermined flow rate threshold value.

20 Claims, 3 Drawing Sheets

(56) References Cited

U.S. PATENT DOCUMENTS

| | | | |
|---|---|---|---|
| 2005/0094704 A1* | 5/2005 | De Cicco et al. | 374/120 |
| 2005/0154345 A1* | 7/2005 | Milleker | A61M 1/3663 604/67 |
| 2008/0021377 A1 | 1/2008 | Kienman et al. | |
| 2009/0012655 A1 | 1/2009 | Kienman et al. | |
| 2010/0022937 A1 | 1/2010 | Bedingfield et al. | |
| 2010/0038322 A1 | 2/2010 | Hedmann et al. | |
| 2011/0098625 A1* | 4/2011 | Masala | A61M 1/342 604/6.09 |
| 2011/0186517 A1 | 8/2011 | Hedmann et al. | |

FOREIGN PATENT DOCUMENTS

| | | |
|---|---|---|
| DE | 10 2009 060 330 | 6/2011 |
| EP | 0 254 801 | 2/1988 |
| EP | 0 956 876 | 11/1999 |
| EP | 1 195 171 | 4/2002 |
| WO | WO 03/099354 | 12/2003 |
| WO | WO 2007/084703 | 7/2007 |

* cited by examiner

APPARATUS FOR HEATING A MEDICAL FLUID

CROSS-REFERENCE TO RELATED APPLICATIONS

This application claims the benefit of U.S provisional application No. 61/497,149, filed Jun. 15, 2011, which claims the priority of German number 10 2011 104 218.4 filed Jun. 15, 2011, hereby incorporated by reference.

BACKGROUND OF THE INVENTION

1. Field of Invention

The present invention relates to an apparatus for heating a medical fluid, a method for heating a medical fluid, and a blood treatment device.

2. Description of the Prior Art

In the extracorporeal blood treatment it is necessary to temper the processed fluids, in order to prevent cooling down of the patient. In the extracorporeal dialysis treatments of the blood the dialysis fluid, or further fluids, such as e.g. substitution fluids, generally are brought to a corresponding temperature, in order to prevent the blood in the extracorporeal circuit from cooling down too much.

The tempering of dialysis fluids also can be found in treatment systems of the peritoneal dialysis. The dialysis fluid is administered into the peritoneum of the patient and must be tempered correspondingly. Various treatment modes are known, in which the dialysis fluid must be supplied to the patient according to automated flow schemes and the dialysis fluid must be tempered corresponding to the flow scheme.

Both in the hemodialysis and in the peritoneal dialysis, systems are under development and already state of the art, in which hydraulic and thermal functional elements for processing the dialysis fluid or other physiological fluids, such as e.g. substitution fluid (EN), are provided on disposable articles. The use of disposable articles, which generally are made of plastics, imposes particular requirements on the control of the heat source.

It should be noted that the temperature control of fluids in disposable articles is a slow process. The poor heat transfer in the disposable article in addition requires high temperatures at the heater interface. So, it is not uncommon that a fluid temperature of 40° C. requires a temperature of the heating plate of more than 80° C.

When the flow is interrupted due to the process or an alarm, the fluid is present at the hot interface and can be overheated. This can lead to the fact that the heater is or must be switched off in the case of a flow standstill. During short standstill times overheating and hence a condition requiring an alarm nevertheless can occur. During long standstill times, the fluid will cool down more.

EP 0 956 876 A1 discloses a disposable cassette for the peritoneal dialysis for delivering and tempering the dialysis fluid.

US 2009/012655 A1 discloses a controlled heating element for tempering dialysis fluid on a dialysis cassette. The heating element is actuated on the basis of a temperature deviation and the flow rate of the dialysis fluid.

EP 0 254 801 B1 discloses a fluid heater with means for determining the fluid temperature, the heater temperature and the temperature of an interconnected heating plate. Switching off is effected when heater or heating plate are too hot, in particular when there is a strongly reduced flow of the fluid.

SUMMARY OF THE INVENTION

Therefore, it is the object of the present invention to develop an apparatus, a method and a blood treatment device as mentioned above in an advantageous way, in particular to the effect that overheating of the medical fluid to be used and to be heated, in particular of the dialysate or other substitution solutions, can safely be avoided.

In accordance with the invention, this object is solved by an apparatus with the features described herein. Accordingly, it is provided that an apparatus for heating a medical fluid, in particular a dialysis fluid, comprises at least one fluid passage for delivering the medical fluid, at least one heating element by means of which the medical fluid in the fluid passage can be heated, at least one first detection means for detecting a parameter which correlates with the flow rate of the medical fluid through the fluid passage, and/or at least one second detection means for detecting a parameter which corresponds to a set point for the flow rate of the medical fluid through the fluid passage, at least one control and/or regulating means by means of which the fluid temperature of the fluid in the fluid passage and/or the temperature of the heating element can be controlled and/or regulated, and a switching means by means of which the control and/or regulating means can be switched from a fluid temperature control to a heating element temperature control and/or vice versa, wherein the switching means is designed such that switching is effected when it is detected by means of the switching means that the flow rate falls below and/or exceeds a predetermined flow rate threshold value.

In particular, this involves the advantage that the temperature of the medical fluid can be controlled in a safe and simple way even in the case of a flow standstill. In addition, an acceleration of the control of the fluid temperature is effected after a flow standstill. Furthermore, it is possible particularly advantageously to achieve a reduction of the undertemperature of the medical fluid even after long standstill times. Furthermore, it is advantageously possible to achieve an avoidance of conditions requiring an alarm in the case of a flow standstill due to overheating.

A fluid temperature control in particular is a control of the temperature of the fluid in the fluid passage to the effect that the temperature existing there is adjusted to a set point.

A heating element temperature control in particular is a control of the temperature of the heating element to the effect that the temperature existing there is adjusted to a set point.

These set points each are chosen corresponding to the respective requirements. For example, the fluid temperature set point can be chosen in dependence on the flow rate of the fluid through the fluid passage, in particular be chosen such that the fluid has a physiological temperature, e.g. in the range between 35° C.-37° C. The heating element for example can have a temperature of distinctly above 80° C.

The heating element temperature set point furthermore can be chosen such that even with a fluid standstill in the fluid passage overheating of the fluid safely is avoided. For this purpose, for example a heating element temperature set point of not more than 50° C. can be chosen. Possible temperature set points above all can lie in the temperature range between 30° C. and 50° C.

The predetermined flow rate threshold value, where on exceeding or falling below the same switching is effected from a fluid temperature control to a heating element control, for example can be a flow rate of zero. In principle, however, it is also possible to be able to freely choose this parameter. In particular, it is conceivable to choose the flow rate threshold value such that on falling below this threshold value switching to a heating element temperature control is required, in order to avoid overheating.

Furthermore, it can be provided that the apparatus furthermore comprises at least one delivering means for delivering the medical fluid through the fluid passage and/or at least one first means for detecting a parameter which correlates with the temperature of the heating element and/or at least one second means for detecting a parameter which correlates with the temperature of the medical fluid in the fluid passage and/or at least one third means for detecting a parameter which correlates with the flow rate of the medical fluid through the fluid passage and/or at least one fourth means for detecting a parameter which corresponds to a set point for the flow rate of the medical fluid through the fluid passage. The first means for detecting a parameter which correlates with the temperature of the heating element and/or at least one second means for detecting a parameter which correlates with the temperature of the medical fluid in the fluid passage for example can be temperature sensors.

Furthermore, it is possible that the control and/or regulating means comprises at least one checking means by means of which the fluid temperature can be checked with reference to a parameter which correlates with the fluid temperature and/or at least one second checking means by means of which the heating element temperature can be checked with reference to a parameter which correlates with the temperature of the heating element.

It is conceivable that the heating element is a resistance heater.

It can also be provided that the heating element is and/or comprises a radiation source, wherein the radiation source preferably is and/or comprises an infrared radiation source and/or a microwave radiation source.

Furthermore, it is conceivable that the heating element is and/or comprises a Peltier element. By using Peltier elements it can advantageously be achieved that the heating element can also be cooled, so that reaching the setpoint temperature of the heating element can be accelerated.

Furthermore, it is possible that after having switched to the heating element temperature control, the heating element is operable in a temperature range from about 40° C. to 50° C., in particular in a temperature range from about 42° C. to 46° C.

In addition, it can be provided that the third means for detecting a parameter which correlates with the flow rate is a detection means by means of which the delivery rate of the delivering means for delivering the medical fluid through the fluid passage can be detected.

Preferably, it is possible that the delivering means is a peristaltic pump, in particular a peristaltic hose pump and/or a positive-displacement pump.

Furthermore, the present invention relates to a method for heating a medical fluid with the features described herein. Accordingly, it is provided that in a method for heating a medical fluid, in particular a dialysis fluid, the medical fluid is delivered through a fluid passage, wherein the medical fluid is heated in the fluid passage, wherein the fluid temperature of the medical fluid in the fluid passage is monitored, and wherein the heating element temperature is monitored, wherein switching is effected from a fluid temperature control to a heating element temperature control or vice versa, when it is detected that the flow rate falls below or exceeds a predetermined flow rate threshold of the delivery of the medical fluid through the fluid passage.

Furthermore, it can be provided that the method is carried out with the aforementioned apparatus as described herein.

Furthermore, the present invention relates to a blood treatment device, in particular a dialysis machine or a peritoneal dialysis machine, that comprises at least one apparatus as described herein.

The blood treatment device in particular can be a dialysis machine or peritoneal dialysis machine.

In addition, it can be provided that by means of the blood treatment device, the method as described herein can be carried out.

BRIEF DESCRIPTION OF THE DRAWINGS

Further details and advantages of the invention will now be explained in detail with reference to an exemplary embodiment illustrated in the drawing, in which.

DETAILED DESCRIPTION OF THE PREFERRED EMBODIMENTS

Figure 1:
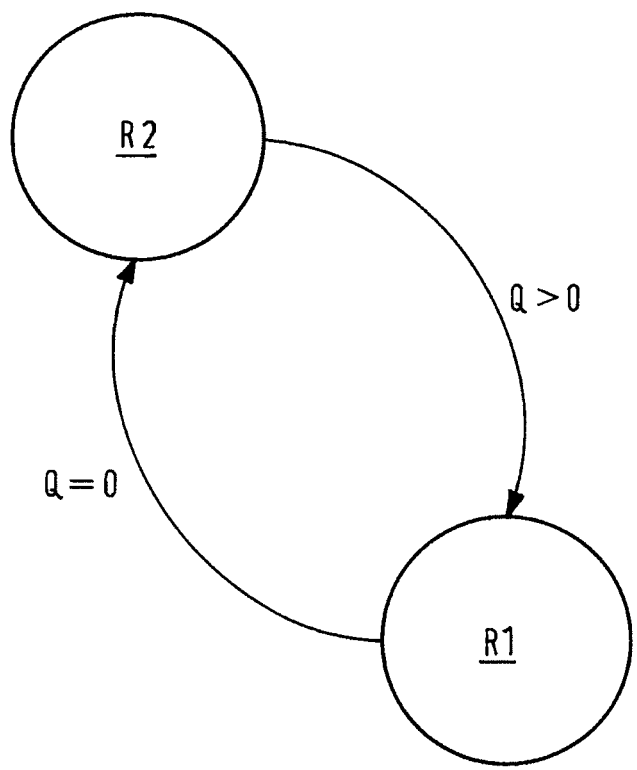
FIG. 1: shows a schematic representation of the control logic.

FIG. 1 shows a schematic representation of the control logic according to the invention. During a delivery of the dialysis fluid, i.e. during the condition Q>0, a control of the fluid temperature is effected, in FIG. 1 designated with R1. If the condition Q=0 occurs, i.e. no more dialysis fluid F is delivered, the system switches over to a control of the heating plate temperature. In FIG. 1, this condition of the control of the heating plate temperature is designated with R2.

The control of the heating element 20 (cf. FIGS. 2 to 4) thus is oriented to the flow conditions of the dialysis fluid. If a delivery condition of the dialysis fluid exists, the control unit takes the initial fluid temperature as measured quantity, compares the same with the specified setpoint temperature and correspondingly actuates the heating element.

If a standstill of the fluid delivery exists, the controller takes the measured temperature of the heating element 20 as measured quantity, compares the same with a specified setpoint temperature of the heating element 20 and correspondingly actuates the heating element 20.

In doing so, further correction factors can be included in the control.

Suitable heating elements in particular include resistance heaters, radiation sources such as infrared radiation sources or microwave radiation sources, and Peltier elements.

If there is no flow through the heater, the control of the fluid temperature is changed into a control of the heating plate temperature. The same can be adjusted for example to a value of 42° C. or 46° C., in order to in any case avoid an alarm due to overtemperature of the fluid when the fluid pump is restarted. However, in particular when using disposable articles it can also lie above this value, as due to the low thermal conductivity of the used plastic materials this temperature does not completely arrive at the fluid.

By using Peltier elements it can advantageously be achieved that the heating plate can also be cooled, so that reaching the setpoint temperature of the heating plate can be accelerated.

A control of the temperature of fluids in disposable articles or also in permanently installed lines is possible.

To monitor the delivery condition, a direct measurement of the flow through the fluid passage can be effected or a use of specified values of the operating and/or protection system can be effected for triggering the switching of the control quantity.

Figure 2:
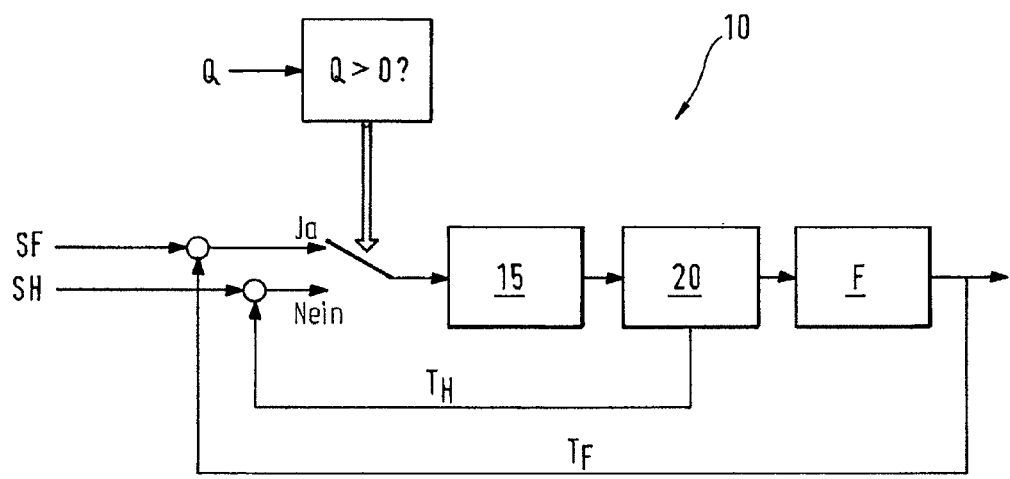
FIG. 2: shows a first block circuit diagram of the control according to the invention.

FIG. 2 schematically shows the control circuit in a first embodiment of the apparatus 10 for heating a medical fluid F. As shown in FIG. 2, the flow rate Q is monitored, namely as to whether the condition Q>0 exists. The control and/or regulating unit 15 here is realized by a controller 15. If this is the case, an adjustment of the heater 20 to the setpoint temperature SF of the fluid F is effected by means of the controller 15. It the condition Q>0 is not satisfied any more, an adjustment to the setpoint temperature SH of the heating plate 20 is effected by means of the controller 15, so that the fluid F cannot be overheated by means of the heater 20. The heating plate temperature is designated with $T_H$ and the fluid temperature is designated with $T_F$.

Figure 3:
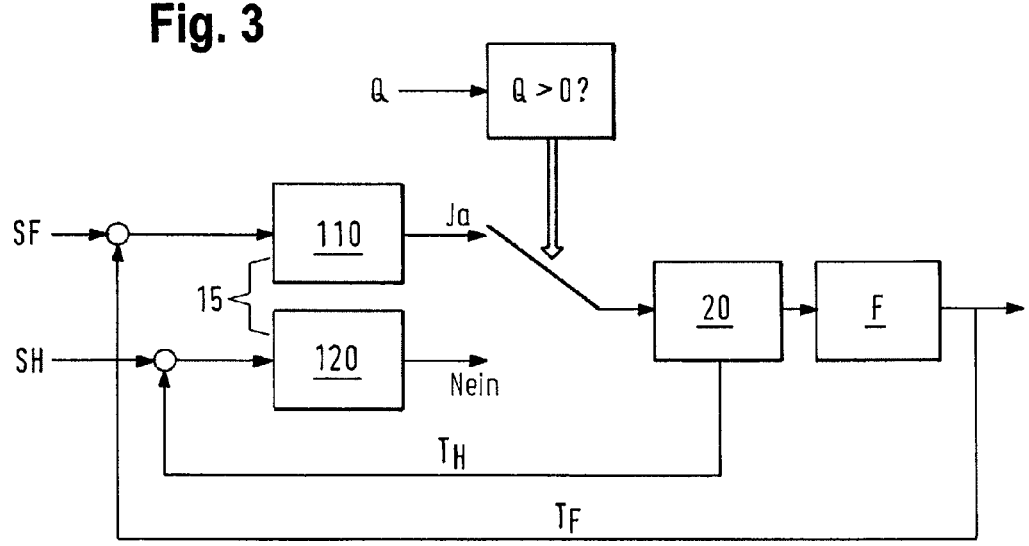
FIG. 3: shows another block circuit diagram of the control according to the invention in a second embodiment.

FIG. 3 shows another configuration of the control according to the invention. Here as well, the condition Q>0 is monitored. However, a separate controller 110 for the control R1 of the fluid temperature $T_F$ and a separate controller 120 for the control R2 of the heating plate temperature $T_H$ are provided here, by means of which the heater 20 can each be adjusted correspondingly for tempering the fluid F. Here, the controllers 110 and 120 form the control and/or regulating unit 15. If the condition Q>0 exists, a control by means of the controller 110 is effected. If the condition Q=0 occurs, a control of the heater 20 by means of the controller 120 is effected, so that a control R2 of the heating plate temperature $T_H$ is effected.

Figure 4:
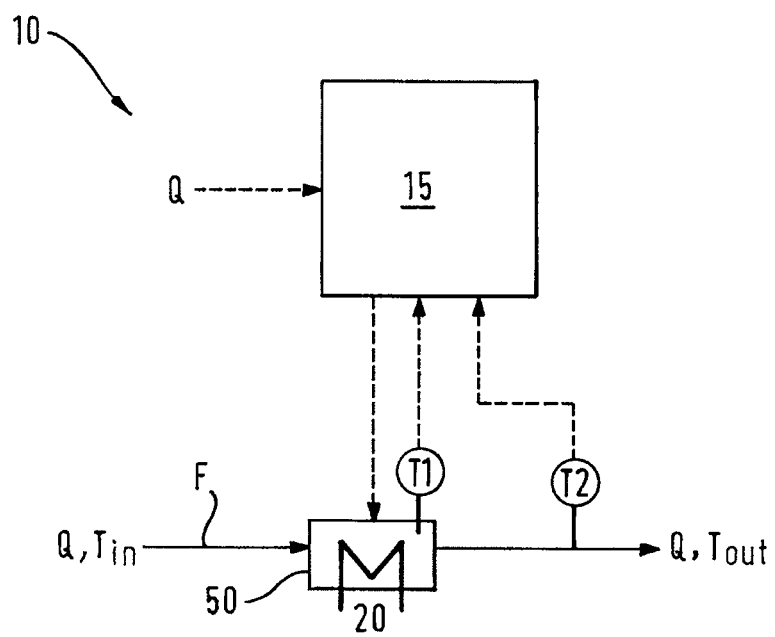
FIG. 4: shows a schematic representation of the apparatus according to the invention for heating a medical fluid, here the dialysis fluid.

FIG. 4 shows a schematic view of the apparatus 10 of the invention for heating a dialysis fluid F which flows through the fluid passage 50, in which the heater 20 is arranged, with a flow rate Q and an inlet temperature $T_{in}$. By means of a first temperature sensor T1 the detection of the heating plate temperature is effected, which is communicated to a control and/or regulating unit 15. Downstream of the fluid passage 50 a further temperature detection of the dialysis fluid F is effected by means of a further temperature sensor T2, wherein the temperature $T_{out}$ determined there likewise is communicated to the control and/or regulating unit 15.

The non-illustrated pump can be located upstream or downstream of the fluid passage 50 or the heater 20.

In addition, it can be provided that a measurement of the inlet temperature of the fluid F, i.e. the temperature $T_{in}$, is effected and furthermore that a measurement of the flow Q is effected.

A measurement of the flow Q for example can be effected in that the rotational speed of a peristaltic hose pump, by means of which the fluid F is delivered, is determined and communicated to the control and/or regulating means 15.

What is claimed is:

1. An apparatus for heating a medical fluid, comprising:
a fluid passage for delivering the medical fluid;
a heating element for heating the medical fluid in the fluid passage;
a detector, the detector including at least one of
a first detector for detecting a parameter which correlates with a flow rate of the medical fluid through the fluid passage, and
a second detector for detecting to parameter which corresponds to a set point for the flow rate of the medical fluid through the fluid passage;
a controller that can control or regulate a fluid temperature of the medical fluid in he fluid passage and to temperature of the heating element; and
a switching circuit that switches the controller between controlling or regulating the fluid temperature of the medical fluid in the fluid passage and controlling or regulating the temperature of the heating element,
the switching circuit being configured such that the switching is triggered in response to the switching circuit detecting that the flow rate falls below or exceeds a predetermined flow rate threshold value.

2. The apparatus according to claim 1, further comprising a delivering unit for delivering the medical fluid through the fluid passage.

3. The apparatus according to claim 2, wherein the first detector for detecting the parameter which correlates with the flow rate of the medical fluid through the fluid passage detects a delivery rate of the delivering unit for delivering the medical fluid through the fluid passage.

4. The apparatus according to claim 2, wherein the delivering unit includes a peristaltic pump.

5. The apparatus according to claim 4, wherein the peristaltic pump is at least one of a peristaltic hose pump and a positive-displacement pump.

6. The apparatus according to claim 1, further comprising at least one of
a first temperature parameter detector for detecting a parameter which correlates with the temperature of the heating element, and
a second temperature parameter detector for detecting a parameter which correlates with the fluid temperature of the medical fluid in the fluid passage.

7. The apparatus according to claim 1, wherein the controller includes at least one of
a first checking unit that checks the fluid temperature with reference to a parameter which correlates with the fluid temperature, and
a second checking unit that checks the temperature of the heating element with reference to a parameter which correlates with the temperature of the heating element.

8. The apparatus according to claim 1, wherein the heating element includes a resistance heater.

9. The apparatus according to claim 1, wherein the heating element includes a radiation source.

10. The apparatus according to claim 9, wherein the radiation source includes at least one of an infrared radiation source and a microwave radiation source.

11. The apparatus according to claim 1, wherein the heating element includes a Peltier element.

12. The apparatus according to claim 1, wherein, after having switched to controlling or regulating the temperature of the heating element, the heating element is operable in a temperature range from about 37° C. to 60° C.

13. The apparatus according to claim 12, wherein the temperature range is from about 42° C. to 46° C.

14. The apparatus according to claim. 1, wherein the medical fluid is a dialysis fluid.

15. The apparatus according to claim 1, wherein, if the switching circuit, detects that there is substantially no flow of the medical fluid through the fluid passage, such that the flow rate of the medical fluid through the fluid passage is substantially zero, the switching circuit switches the controller from controlling or regulating the fluid temperature of the medical fluid in the fluid passage to controlling or regulating the temperature of the heating element.

16. The apparatus according to claim 15, wherein, after detecting that there is substantially no flow of the medical fluid through the fluid passage and switching the controller to controlling or regulating the temperature of the heating element, if the flow rate subsequently increases above zero, the switching circuit switches the controller back to controlling or regulating the fluid temperature of the medical fluid in the fluid passage.

17. A blood treatment device, comprising:
an apparatus for heating a medical fluid according to claim 1.

18. The blood treatment device according to claim 17, wherein the medical fluid is a dialysis fluid and wherein the blood treatment device is a dialysis machine or a peritoneal dialysis machine.

19. A method of heating a medical fluid with a device having a fluid passage, a heating element, a detector having a least one of a first detector for detecting a parameter which correlates with a flow rate of the medical fluid through the fluid passage, and a second detector for detecting a parameter which corresponds to a set point for the flow rate of the medical fluid through the fluid passage, a controller, and a switching circuit, said method comprising:

delivering the medical fluid through the fluid passage;
heating the medical fluid in the fluid passage using the heating element;
monitoring a fluid temperature of the medical fluid in the fluid passage;
monitoring a temperature of the heating element temperature;
detecting at least one of the parameter which correlates with the flow rate of the medical fluid through the fluid passage, and the parameter which corresponds to the set point for the flow rate of the medical fluid through the fluid passage; and
switching between controlling or regulating the fluid temperature of the medical fluid in the fluid passage and controlling or regulating the temperature of the heating element, the switching being effected after detecting that the flow rate falls below or exceeds a predetermined flow rate threshold value.

20. The method according to claim 19, wherein the medical fluid is a dialysis fluid.

* * * * *